US00PP09693P

United States Patent [19]

Van Rijn

[11] Patent Number: Plant 9,693

[45] Date of Patent: Nov. 12, 1996

[54] CALATHEA PLANT NAMED 'SILVIA'

[75] Inventor: Magdalena J. M. Van Rijn, Am Schipluiden, Netherlands

[73] Assignee: Van Rijn Plants, Am Schipluiden, Netherlands

[21] Appl. No.: 510,494

[22] Filed: Aug. 2, 1995

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

A Calathea plant named 'Silvia' having oval leaves. Young leaves have a purple-red center and mature leaves are bright green with weak purple-red strips parallel to the primary veins which are close to the base of the leaf. The center is bordered by a very dark green margin. The lower side is dull purple-red.

7 Drawing Sheets

The present invention comprises a new and distinct cultivar of Calathea, botanically known as *Calathea roseo* picta and referred to by the cultivar named 'Silvia.'

The new cultivar is a random mutation and was discovered and selected from a group of *C. roseo* picta in April 1989 in Schipluiden, The Netherlands, by the inventor Magdalena J. M. van Rijn.

Propagation by tissue culture at the above noted location increased the number of plants for evaluation and has demonstrated the stability of the combination of characteristics of 'Silvia' from generation to generation.

The following observations, measurements and values were taken at 's-Gravenzande, The Netherlands, and describe plans grown in the Nursery Schipluiden under greenhouse conditions which closely approximate those generally used in horticultural practice.

The following traits have been repeatedly observed to be characteristics which in combination distinguish 'Silvia' from others of the same species.

1. The plant produces leaves with dark green veins and the midrib is purple-red. The margin is green which becomes darker green towards the center of the leaf. The outermost margin of the leaf is purple-red.

2. The amount of purple-red in the center of the leaves varies with the age and maturity of the plant, from entirely purple when juvenile it becomes bright green with stains of purple-red around the primary veins when mature. The lower side of the leaves is dull purple-red.

All color references are to The Royal Horticultural Society Colour Chart (R.H.S.). The color values were determined between 12:00 h and 12:30 h on Apr. 7, 1995 under natural light with a light intensity of 1210 J/m$^2$ at 's-Gravenzande, The Netherlands.

Phenotypic characteristics may vary somewhat depending on horticulural practices such as light level and fertilization rate, among others, without, however, any variance in genotype.

In the accompanying color photographic drawings, a representative plant of 'Silvia', age 9.5 months, grown in a 19 cm pot, is shown.

Sheet 1 is a top perspective of the plant.

Sheet 2 is a top/side perspective.

Sheet 3 is a side perspective.

Sheet 4 shows the upper surface of a young leaf.

Sheets 5 and 6 show the upper surfaces of young to mature leaves.

Finally, sheet 7 shows the upper surface of a mature leaf of 'Silvia'.

Origin: Mutation of *Calathea roseo* picta.

Classification: *Calathea roseo* picta, cv. *Silvia'*.

Propagation: Asexual production either by tissue culture of division.

Plant: Age: 9.5 months Pot size: 19 cm.

*Height.*—45–51 cm.

*Width.*—46–56 cm.

*Branching.*—Good.

*Growth habit.*—Compact.

Leaves:

*Form.*—Ovate, mucronulate tip, entire margins.

*Size.*—Mature about 25 cm long×14 cm wide.

*Petiole.*—Size: Approximately 23 cm–28 cm. Color: R.H.S. 187 A, purple-red.

*Petiole wings.*—Size: Approximately 10 cm long, and 10 mm wide. Color: R.H.S. 187 C (purple-red).

*Geniculum.*—Size: 30–40 mm long and 5–7 mm wide. Color: R.H.S. 177 A.

*Veins.*—Shape: Upper surface: Midrib sunken, leaf blade slightly concave between veins. Lower surface: Midrib protrudes from the lower surface. Color: Midrib at the base is purple-red becoming brighter red toward the leaf tip. Primary veins are dark green.

*Color.*—Upper surface: Young Margin: R.H.S. 136 A, very dark green. Leaf center: R.H.S. 59 C, purple-red with stains of R.H.S. 191 B, bright green. Mature Margin: Outermost margin R.H.S. 137 A, dark green. Leaf center: R.H.S. 139 D, bright green with strips or R.H.S. 59 C, purple-red. Midrib: R.H.S. 59 B, brown-red. Lower surface: R.H.S. 187 A, dull purple-red. Midrib: R.H.S. 175 A-177 A, brown-red. Margin: R.H.S. 187 A, dull purple-red.

Roots: Thin white roots.

General observation: Calathea 'Silvia' has oval leaves. Young leaves have purple-red center, and mature leaves are bright green with weak purple-red strips parallel to the primary veins which are close to the base of the leaf. The center is bordered by a very dark green margin. The lower side is dull purple- red.

| | CLOSEST COMPARISON CULTIVAR | |
|---|---|---|
| Characteristic | Cultivar 'Rosy' | Cultivar 'Silvia' |
| Leaf form | orbicular | oval |
| Leaf tip | mucronate | mucronulate |
| Plant height | 12 to 15 cm | 45 to 51 cm |
| Geniculum length: | approximately 13 mm | 30 to 40 mm |

I claim:

1. A new and distinct cultivar of Calathea plant named 'Silvia,' as illustrated and described.

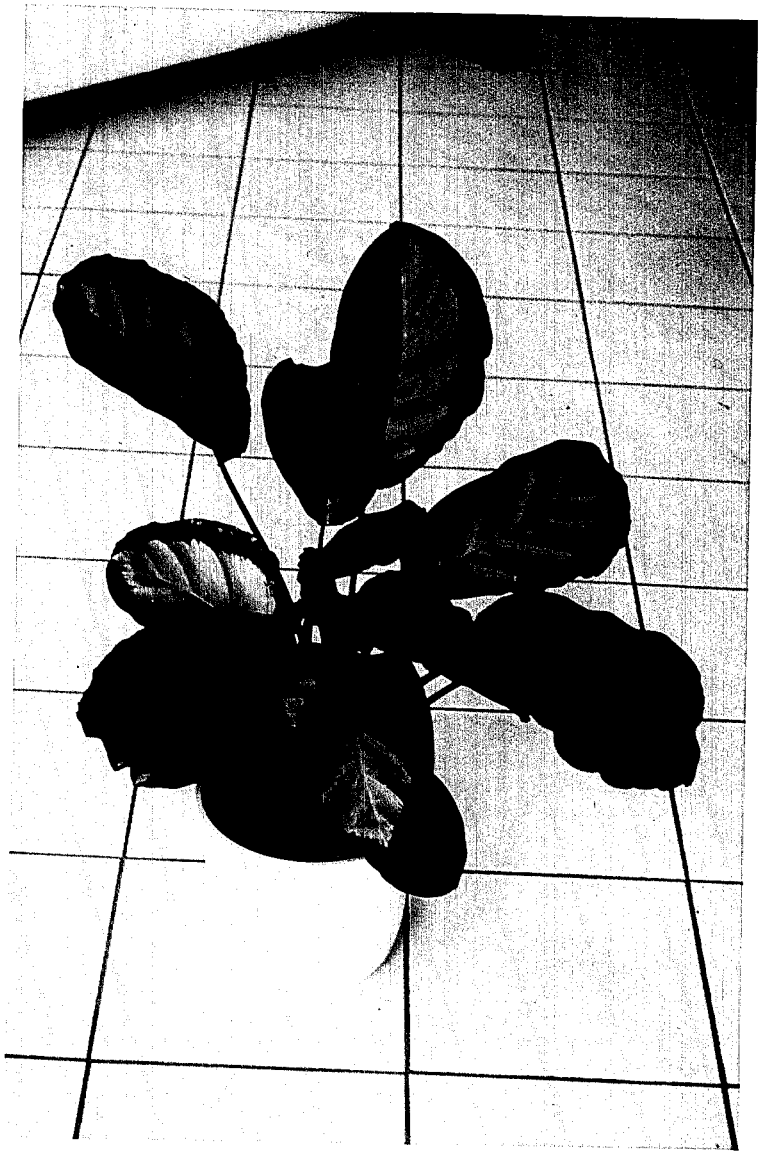

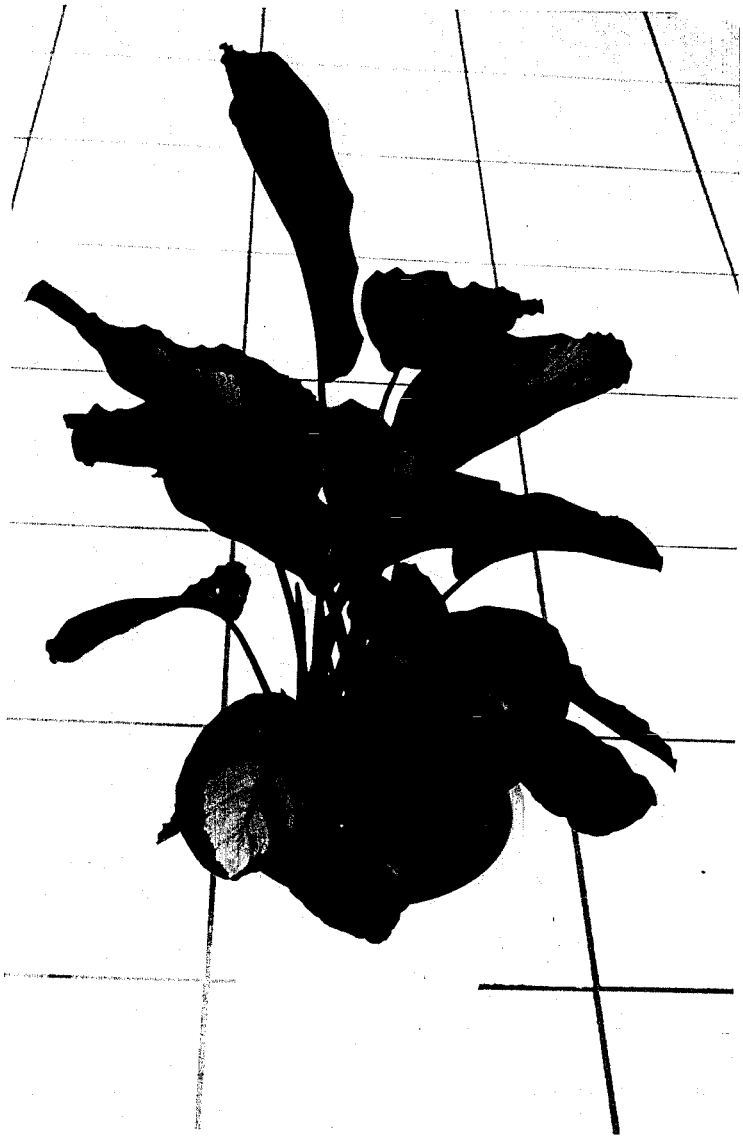

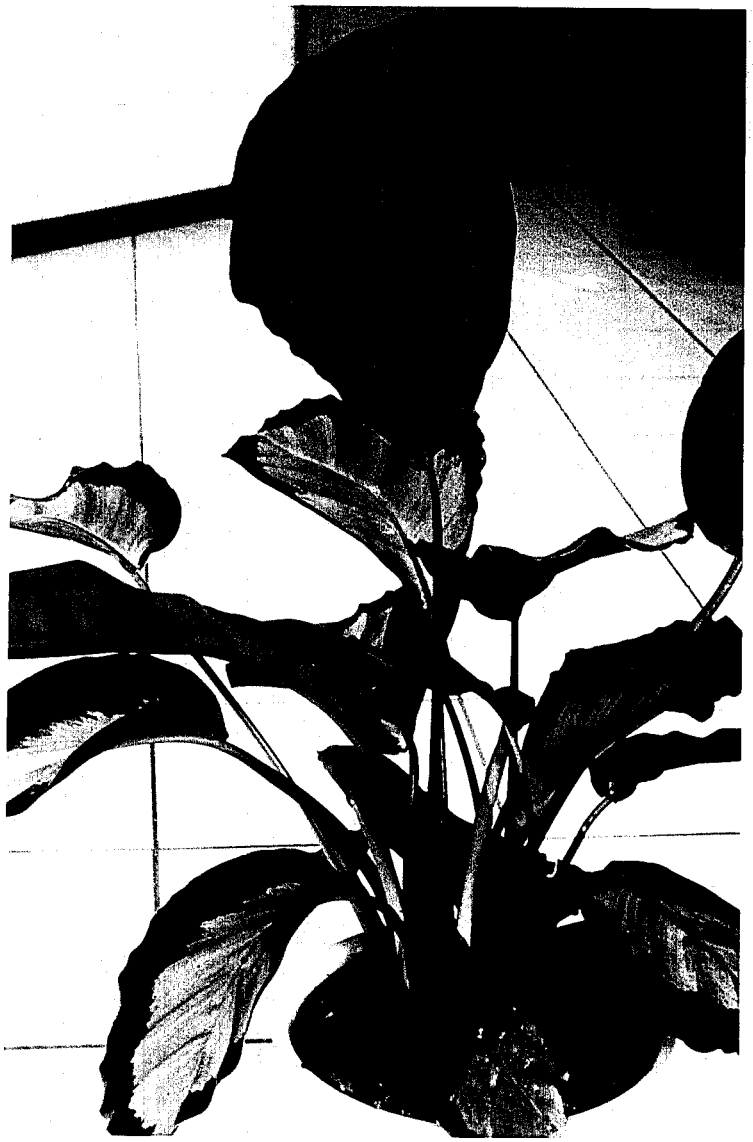

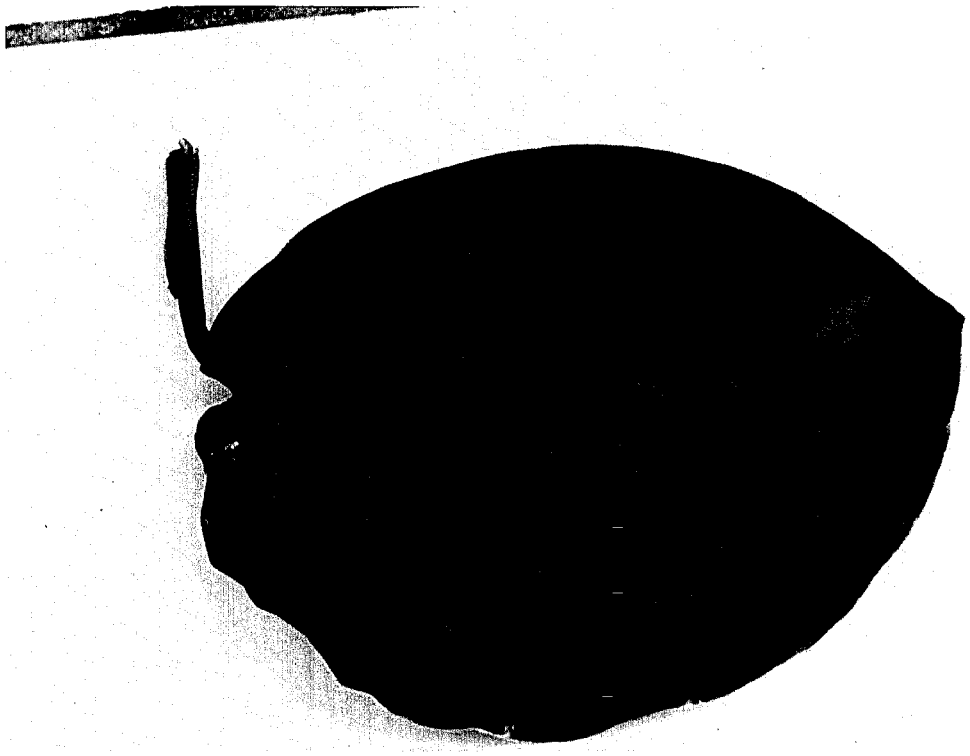

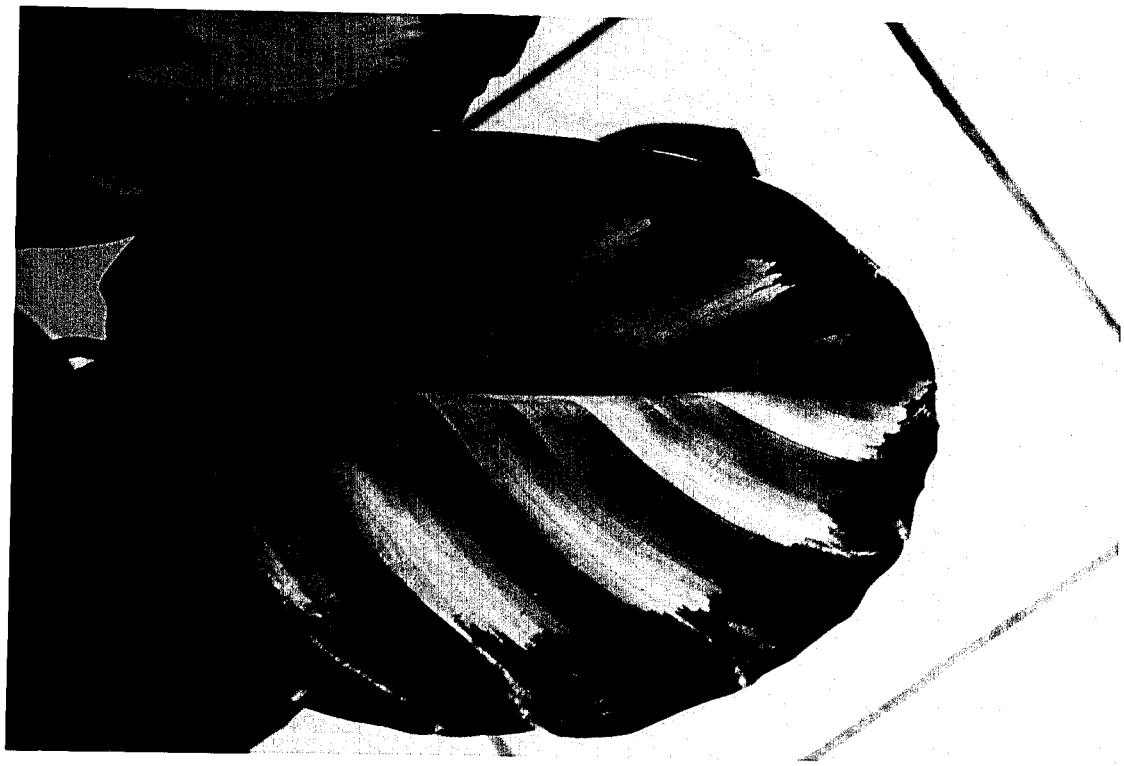

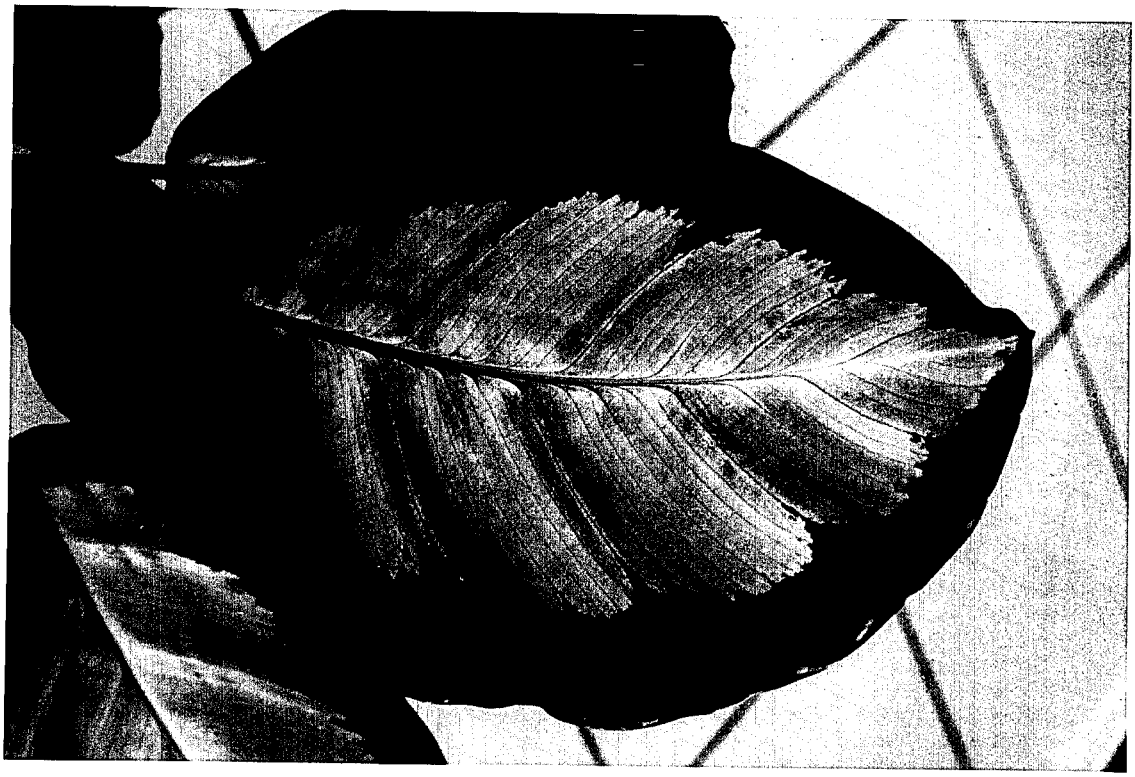

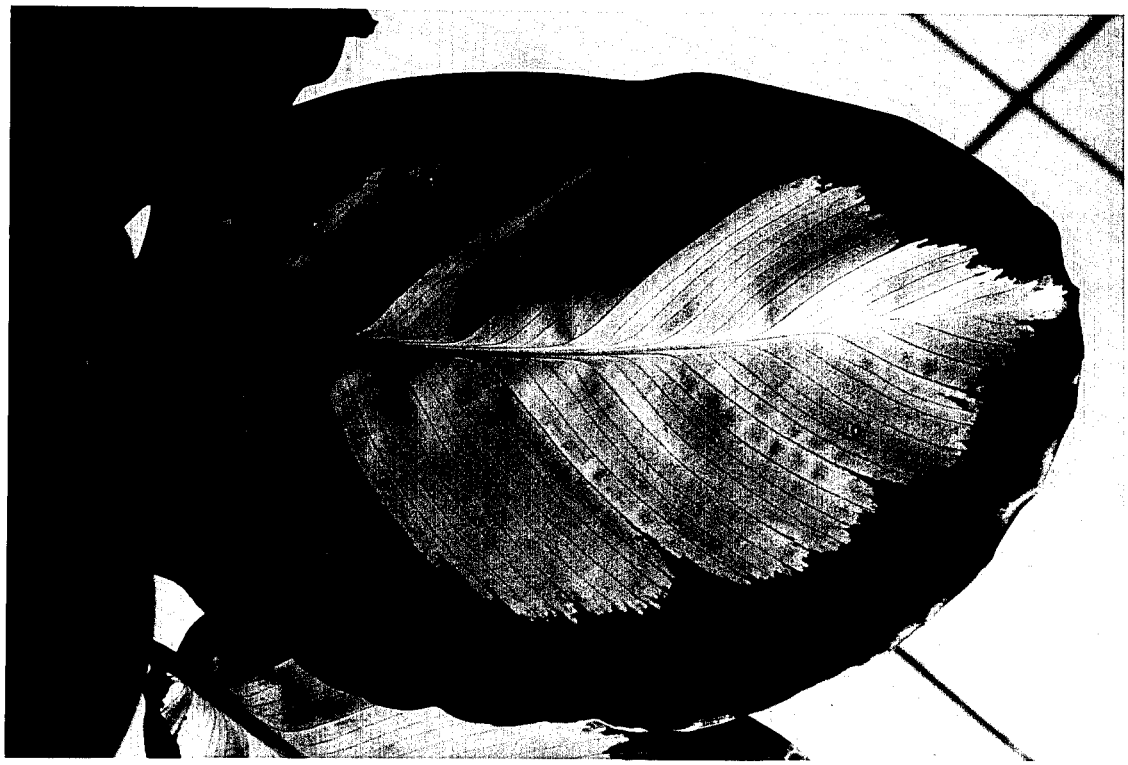

* * * * *